(12) United States Patent
Segall

(10) Patent No.: US 7,564,368 B2
(45) Date of Patent: Jul. 21, 2009

(54) SEMANTIC LIGHT

(76) Inventor: Zary Segall, 23 Pierside Dr., Suite 139, Baltimore, MD (US) 21230

( * ) Notice: Subject to any disclaimer, the term of this patent is extended or adjusted under 35 U.S.C. 154(b) by 276 days.

(21) Appl. No.: 11/800,213

(22) Filed: May 4, 2007

(65) Prior Publication Data

US 2007/0258243 A1 Nov. 8, 2007

Related U.S. Application Data

(60) Provisional application No. 60/797,711, filed on May 4, 2006.

(51) Int. Cl.
*G08B 5/00* (2006.01)

(52) U.S. Cl. ............... 340/815.4; 340/332; 340/691.6; 340/691.1; 340/331

(58) Field of Classification Search ............... 340/332, 340/691.6, 993.5, 691.1, 331
See application file for complete search history.

(56) References Cited

U.S. PATENT DOCUMENTS

| | | | |
|---|---|---|---|
| 7,139,716 B1 * | 11/2006 | Gaziz | 704/275 |
| 7,339,471 B1 * | 3/2008 | Chan et al. | 340/541 |
| 2006/0077193 A1 * | 4/2006 | Thielemans et al. | 345/204 |
| 2006/0149607 A1 * | 7/2006 | Sayers et al. | 705/7 |
| 2006/0227123 A1 * | 10/2006 | Bychkov et al. | 345/204 |

* cited by examiner

*Primary Examiner*—Daryl Pope
(74) *Attorney, Agent, or Firm*—Ober/Kaler; Royal W. Craig

(57) ABSTRACT

A lighting system for delivering a dynamic, fully customized, and automatic illumination to a subject. The lighting system comprises a programmable light unit for emitting a programmed pattern and spectra of illumination, a sensor pod comprising an array of sensors for detecting ambient lighting conditions and subject characteristics, a control unit for allowing a user to program the lighting system, and a processing unit for analyzing data from the sensor pod and control unit to construct an optimal lighting profile in accordance therewith. The lighting system generates light in accordance with the lighting profile which is fully optimized in spectrum, intensity, color, contrast, temperature, angle, and focus for any given environment, subject and task.

8 Claims, 3 Drawing Sheets

SEMANTIC LIGHT

CROSS-REFERENCE TO RELATED APPLICATION(S)

The present application derives priority from U.S. Provisional Application No. 60/797,711 filed May 4, 2006.

BACKGROUND OF THE INVENTION (1) Field of the Invention

The present invention relates to light delivery systems and, more particularly, to a semantic lighting that delivers appropriate light (spectrum, intensity, color, contrast, temperature, angle, focus, data) to a subject by analyzing the properties of the subject (nature, dimensions, shape, texture, contrast, reflectivity, transparence, temperature, etc.), the existing illumination, the eye characteristics of the human user and the relative position of the subject with respect to the source of light and user. In addition, the semantic light delivers dynamic light that is changing in time and in sync with the semantic of the task requiring illumination.

(2) Description of Prior Art

Conventional lighting devices deliver static light and are agnostic to the user, the subject or the environment. Thus, such lighting devices are designed to illuminate a predefined, average illumination scene for an average user. This completely overlooks the fact that the light is perceived differently by different people and that the lighting requirements are different for each particular task. Furthermore the lighting requirement is dependent on the visual qualities of the subject being illuminated. It is well-known that appropriate light can enhance virtually any human experience and make the task at hand easier to perform. Bright light is better for reading, soft warm light for resting, etc. Interior designers recognize this and carefully assess the quality of ambient lighting in a room before installing a lighting system. Along with color, many aspects of a light source help establish task-suitable lighting. Intensity, direction and angle, number of lights, and shadows all play a major role in defining the lighting quality of a scene. Lighting is a key element in human performance and productivity. Thus, good interior designers consider all aspect of the light needed to properly illuminate a room, including intensity, spectrum, directionality, etc. Unfortunately, once the lights are installed they are relatively static. Despite changing seasons, daylight hours, moving occupants of the house, rearranged furniture, etc., conventional lighting does not adapt.

It would be greatly advantageous to provide a dynamic light system (changing in time and in sync with the task performed), a semantic lighting system (adapting to the illuminated subject visual properties), both personalized (adapting to the eye characteristic of the user) and task specific (adapting to the requirement of a particular task), for delivering appropriate light to a subject by controlling a range of variables (spectrum, intensity, color, contrast, temperature, angle, focus, data).

SUMMARY OF THE INVENTION

It is therefore, an object of this invention to provide a dynamic light system that changes its illumination in time and in sync with the task performed.

It is another object to provide a semantic lighting system that adapts to an illuminated subject's visual properties.

It is another object to provide a semantic lighting system that is both personalized (adapting to the eye characteristic of the user) and task specific (adapting to the requirement of a particular task).

It is still another object to provide a semantic lighting system that delivers an appropriate light to a subject by controlling a range of variables (spectrum, intensity, color, contrast, temperature, angle, focus, data).

These and other objects are accomplished herein by a dynamic light system that automatically analyzes a range of properties in order to control a range of variables. The properties analyzed include the proprieties of a subject (nature, dimensions, shape, texture, contrast, reflectivity, transparence, temperature, etc.), plus the properties of the environment (such as existing illumination), plus human properties including eye characteristics and the relative position of the subject with respect to the source of light.

The foregoing properties are automatically analyzed to control a range of variables (spectrum, intensity, color, contrast, temperature, angle, focus, data) in order to project the optimal lighting conditions for any given environment, user, subject and situation. Moreover, the invention disclosed herein provides dynamic light that changes over time to adapt to changing environments and changing requirements of the task requiring illumination.

Other variations and advantages are described in the detailed description below.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

The present invention is an active lighting system that analyzes a subject (by measuring a range of properties of a subject, inclusive of nature, dimensions, shape, texture, contrast, reflectivity, transparence, temperature, etc.), analyzes the environment (by measuring properties such as existing illumination), incorporates a knowledge of the eye characteristics of the user, understands the task the user is performing, and provides the most appropriate lighting conditions for any given environment and situation by automatic control of a range of variables (spectrum, intensity, color, contrast, temperature, angle, focus, data). Since the user is human, properties specifically include the user eye characteristics, relative position of the subject with respect to the source of light, etc.

Not only does the system provide lighting best suited to environment and task, but also provides dynamic lighting that is adjusted over time to adapt to changing environmental and task requirements.

Figure 1:
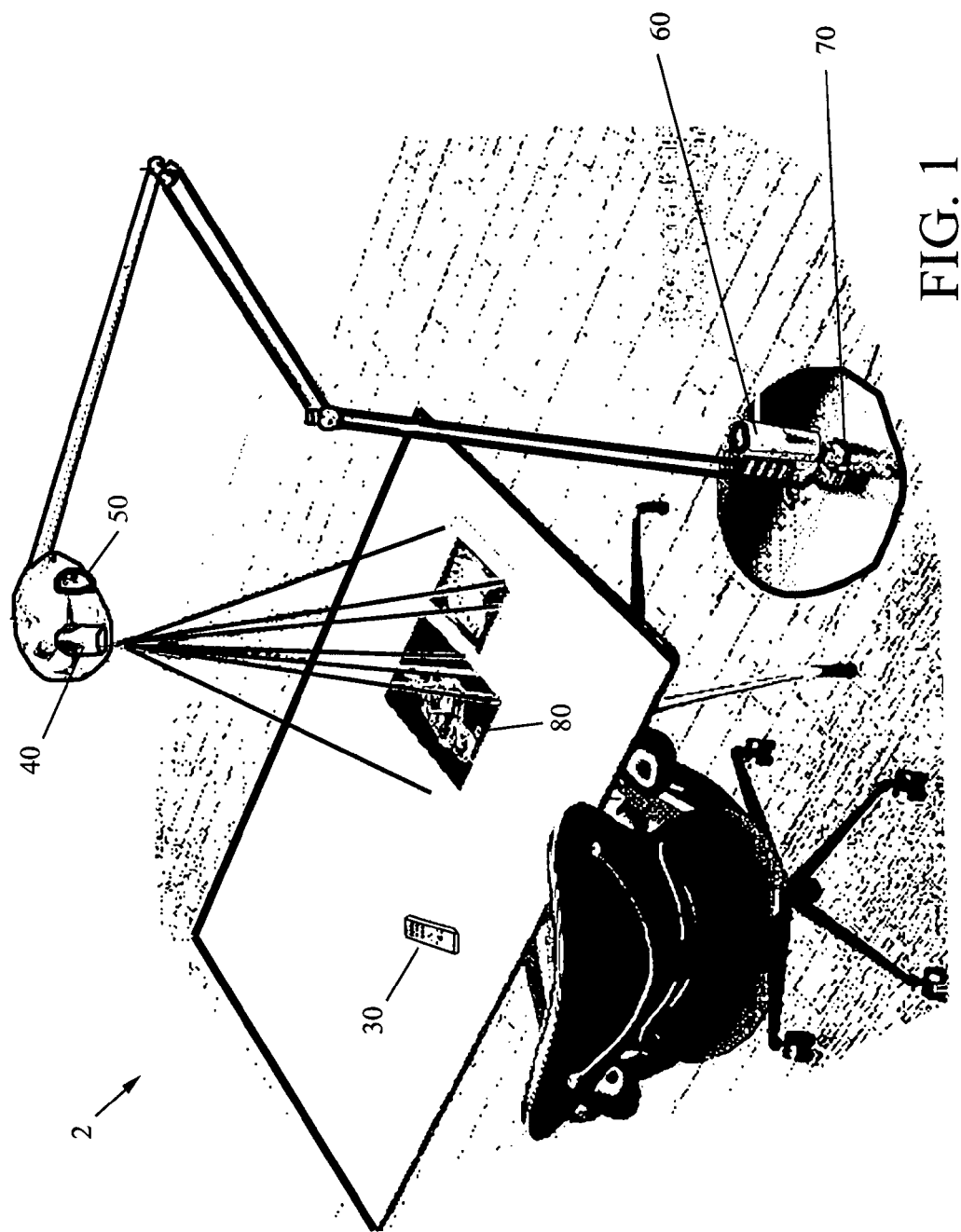
FIG. 1 is a perspective view of the semantic lighting system 2 according to the present invention.
Figure 2:
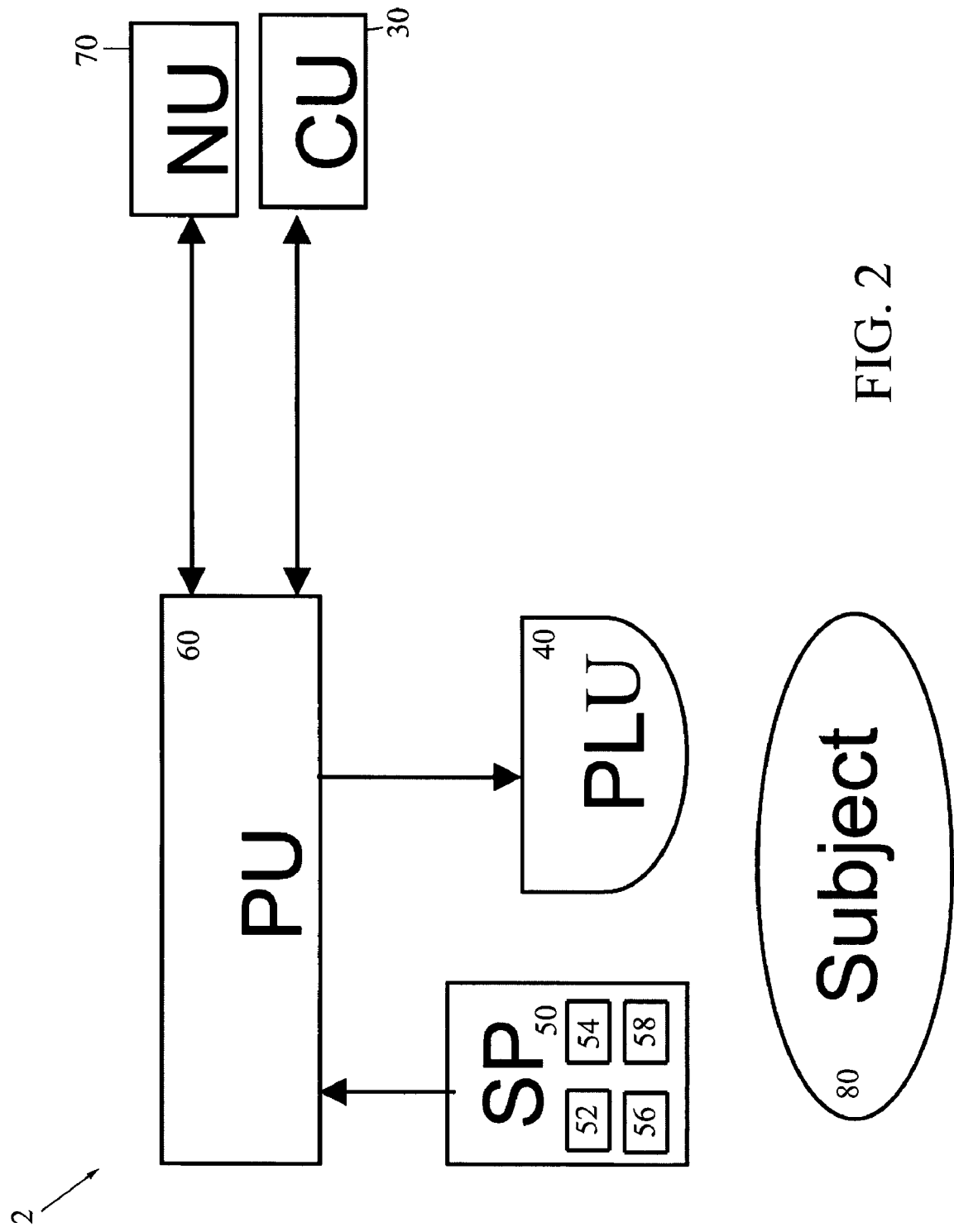
FIG. 2 is a block diagram of the primary components of the semantic lighting system 2 of FIG. 1.

FIG. 1 is a perspective view, and FIG. 2 is a block diagram of the primary components of the semantic lighting system 2 according to the present invention. The system 2 generally includes a Programmable Light Unit 40 (PLU), Sensor Pod 50 (SP) and Control Unit 30 (CU), all of which are available for sensing and controlling the appropriate lighting conditions in a given area for a given subject.

In addition, the system 2 includes a Processing Unit 60 (PU) and Network Unit 70 (NU). The Subject 80 is the target of illumination such as a magazine or a book.

The Sensor Pod (SP) 50 incorporates a variety of sensors including, but not limited to, a visual spectrum camera 52, infrared spectrum camera 54, range sensors 56, a sensor for tracking eye movement 58, and other possible sensors.

The Programmable Light Unit 40 (PLU) preferably includes one or more digital programmable light sources such as a conventional DLP or LCD projectors, one or more high intensity programmable LED clusters, one or more conventional incandescent or fluorescent light sources including halogen, or any combination of the foregoing. PLU 40 also contains conventional means of focusing and directing light to a particular area of the subject.

The Control Unit 30 (CU) includes a user interface with controls for controlling the PU 60, and may be configured as a conventional IR remote controller. The Control Unit 30 (CU) is used for user-input of a "task requirement" and personalization depending on the particular task or environment that the user desires lighting for. The task requirement may be a categorical choice of task such as user reading lighting, user writing lighting, surgery lighting, working, etc.

The Network Unit (NU) 70 may be any conventional network interface for wired or wireless connection to other remote-programmed devices, including but not limited to other semantic lighting systems, the Internet, or any other programmable devices and wireless devices. Network Unit 70 (NU) provides networking capability with other remote systems or accessories having a like networking capability.

The Processing Unit 60 (PU) includes an on-board (one or more) processors with memory and peripheral communications interfaces for receiving inputs from the Sensor Pod 50 (SP), Control Unit 30 (CU) and Network Unit 70 (NU), and for delivering appropriate outputs to the Programmable Light Unit 40 (PLU), Control Unit 30 (CU) and Network Unit 70 (NU). Thus, the Processing Unit 60 (PU) also includes one or more outputs as appropriate for coupling to the Programmable Light Unit 40 (PLU), including, for example, a standard data output (USB, serial, parallel, etc.).

There is software resident on the Processing Unit 60 (PU) that creates an array of models inclusive of a user eye model, task model, and subject model. The user eye model is constructed using specific user physiological eye parameters such as, light perception, color perception, age, eye injury, and lens prescription. The data necessary to construct the user eye model may be pre-programmed or input by the user via Control Unit 30 (CU). The task model is built using a specific categorical task description such as reading, writing or a specific manufacturing task. The data necessary to construct the task model is typically an input by the user via Control Unit (CU). The subject task model is a 2D/3D model of the subject including existing illumination, the shape of the subject, contrast, temperature, color, transparency, reflection and texture.

Given the three completed models, the software resident in the Processing Unit 60 (PU) executes a suite of algorithms that analyze data inputs from the Sensor Pod 50 (SP) (and, optionally, Control Unit 30 (CU) data and Network Unit 70 (NU) data) in accordance with the user eye model, the task model, and subject model, to create a Subject Illumination Profile comprising a set of instructions to control the Programmable Lighting Unit 40 (PLU) in order to produce at any given time light with specified spectrum, intensity, focus, color, contrast, temperature and angle. In addition, if the task model so requires, the PLU 40 will project text and images for aesthetic value or task oriented value. In addition, the Processing Unit 60 (PU) may deliver outputs to the Control Unit 30 (CU) for user-feedback, and to the Network Unit 70 (NU) for remote control of other networked systems or accessories.

Figure 3:
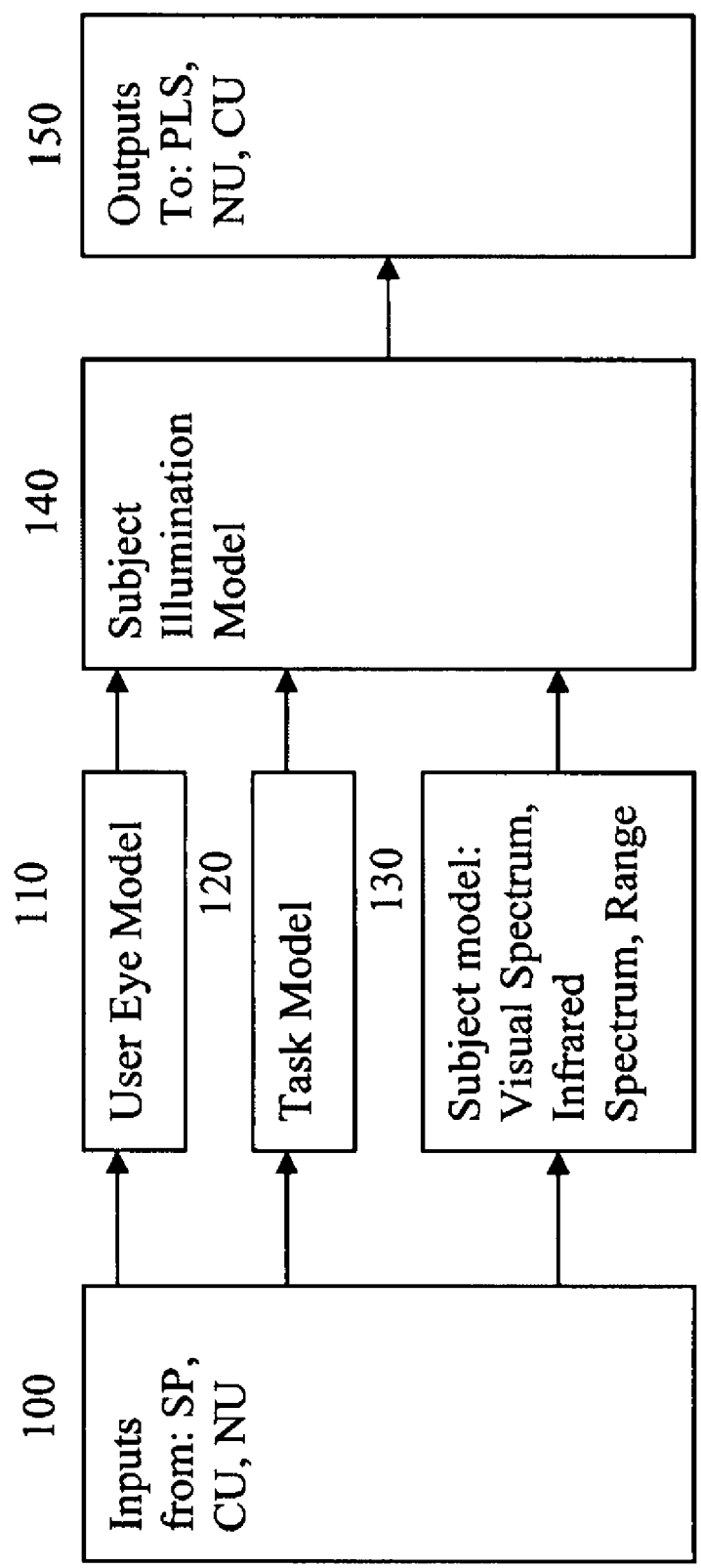
FIG. 3 is a flow diagram illustrating the general operation of the semantic lighting system according to the present invention.

FIG. 3 is a flow diagram illustrating the general operation of the semantic lighting system 2 according to the present invention. In operation, the Processing Unit 60 (PU) receives programming inputs from the Control Unit 30 (CU), plus sensor inputs from the Sensor Pod 50 (SP) which may comprise spectral analyses from the visual spectrum camera 52, infrared spectral analyses from spectrum camera 54, subject range data from range sensors 56, eye tracking information from the tracking device 58, etc. The processor Processing Unit 60 (PU) may additionally receive sensor inputs from the Network Unit 70 (NU), and deliver appropriate outputs to the foregoing devices. The Processing Unit 60 (PU) will execute its internal algorithms as appropriate on the data from the Sensor Pod 50 (SP), and will determine the most appropriate lighting conditions and or text to display based on the user eye model, the task requirement (which may be programmed at Control Unit 30 (CU)), and the subject model 80 (including visual spectrum, infrared spectrum, range, etc.). Additionally, Network Unit 70 (NU) data may be considered.

The Processing Unit 60 (PU) algorithms analyze the combined data, generate the most appropriate Lighting Profile, and outputs control signals to the Programmable Light Unit 40 (PLU) as necessary to control the stated lighting variables (spectrum, intensity, color, contrast, temperature, angle, etc.). In addition, it is envisioned that use of DLP projector(s) will allow text projecting capabilities such as projection of recipes in a kitchen, directions for repair, etc. Like outputs may be delivered to the Control Unit 30 (CU) for visual confirmation, and to the Network Unit (NU) 70 for remote control of networked systems and accessories.

To further understand the various embodiments of the present invention the following are examples of certain application, though the list is not exhaustive:

Task light (as shown in FIG. 1):

In this application the semantic lighting system 2 delivers light that has the most comfortable color, spectrum intensity and temperature for a user that is reading/writing and/or manipulating objects related to a task all collocated on a desk. The subject 80 is a collection of reading/writing materials and objects that are on a work desk. The user is the person that is using the desk. The semantic lighting system 2 takes into consideration the particular user eye performance parameters, the subject position, angle, contrast, texture, color, reflection and the distribution of objects on the desk. Based on the above considerations the Processing Unit 60 (PU) analyzes the data, builds models for the subject and the user, and instructs the Programmable Light Unit 40 (PLU) to deliver appropriate light to each part of the subject. Since in one implementation the Programmable Light Unit 40 (PLU) uses a data projector, in this case the semantic light is a projected image over the subject that could include text that possibly will be used to communicate with the user. Since, the Sensor Pod 50 (SP) is continuously analyzing the subject, user movements, change of lighting condition, change of subject and some user gestures (such as writing, hands movement, moving of objects on the desk, pointing to different part of the subject) are registered and employed as inputs to adjust the Programmable Light Unit (PLU) image.

Reading Light:

In this application the semantic lighting system delivers light that has the most comfortable color, spectrum intensity and temperature for a reading user. The subject is an instance of a reading material (book, magazine, etc.). The semantic lighting system 2 will take in consideration particular user eye performance parameters, the subject position, angle, contrast, texture, color, reflection, the distribution of text/pictures, and the character set. Based on the above considerations the Processing Unit 60 (PU) analyzes the data, builds models for the subject and the user, and instructs the Programmable Light Unit 40 (PLU) to deliver appropriate light to each part of the subject. Since in one implementation the Programmable Light Unit 40 (PLU) uses a data projector unit, in this case, the semantic light is a projected image over the subject that could also include the text to be read, or any other text for communicating with the user. The present system continuously analyzes the subject, user movements, change of lighting condition, change of subject and some user gestures (such as pointing to different part of the subject), and all these are registered and used as input to adjust the PLU image.

Dining Room Light:

In this application the semantic lighting system 2 delivers light that has the most comfortable color, spectrum intensity and temperature for users that are collocated around a dinning table. The subject 80 is a collection of objects that are on a dinning table. The users are the people that are using dining table. The semantic lighting system 2 takes into consideration the subject position, angle, contrast, texture, color, reflection and the distribution of objects on the dining table. Based on the above considerations the Processing Unit 60 (PU) analyzes the data, builds models for the subject, and instructs the Programmable Light Unit 40 (PLU) to deliver appropriate light to each part of the subject. Since in one implementation Programmable Light Unit 40 (PLU) uses a data projector unit, in this case the semantic light is a projected image over the subject that may also include text. Since, the semantic lighting system is continuously analyzing the subject, user movements, change of lighting condition, changes of subject are registered and employed as inputs to adjust the Programmable Light Unit (PLU) image.

Office/Room Semantic Light:

In this application semantic lighting system 2 delivers light that has the most comfortable color, spectrum intensity and temperature for a room. The subject 80 is a collection of objects that are in a room. The users are the people that are using the room. The semantic lighting system 2 takes into consideration the subject position, angle, contrast, texture, color, reflection and the distribution of objects in a room. Based on the above considerations the Processing Unit 60 (PU) analyzes the data, builds Processing Unit 60 (PU) models for the subject, build models for the expected user task in the room and instruct the Programmable Light Unit 40 (PLU) to deliver appropriate light to each part of the subject. Since in one implementation Programmable Light Unit 40 (PLU) uses a collection of clusters of LED high intensity lights that could be programmed in terms of color, temperature, spectrum and color, the semantic light is differentiated for each part of the subject. Since, SP is continuously analyzing the subject, user movements, change of lighting condition, change of subject are registered and employed as inputs to adjust the PLU image.

Surgery Theater Illumination:

In this application the semantic lighting system 2 delivers light that has the most effective color, spectrum intensity and temperature for a physician that is performing a surgery in a surgery room. The subject 80 is the human body that is under the medical procedure. The semantic lighting system 2 takes into consideration particular user eye performance parameters, the particular body part or organ position, range, angle, contrast, texture, color, reflection and other visual properties that are related to the task. Based on the above considerations the Processing Unit 60 (PU) analyzes the data, builds models for the subject and the user, and instructs the Programmable Light Unit 40 (PLU) to deliver appropriate light to each part of the subject. Since in one implementation Programmable Light Unit 40 (PLU) uses a data projector unit, in this case the semantic light is a projected image over the subject that could also include text that could be used to communicate with the user by projecting physiological data directly on the subject. Since the semantic lighting system 2 continuously analyzes the subject, user movements, change of lighting condition, change of subject and some user gestures (such as pointing to different part of the subject) are registered and used as input to adjust the Programmable Light Unit 40 (PLU) light. In addition a wearable semantic light unit may be mounted on the forehead of the user to direct the Programmable Light Unit 40 (PLU) to deliver appropriate light that is controlled by user head movement.

In addition to the foregoing, the semantic lighting system lends itself to specific medical procedures. Using the same principles as in the Surgery theater illumination, semantic lighting system may be adapted for specific medical procedures. The same is true for specific manufacturing jobs. This application is similar to that of task lighting (above) but may also include a manufacturing task model. For example, the algorithms may employ additional models for a lathe, for the manufactured part, the manufacturing process, etc. Moreover, the Programmable Light Unit (PLU) may project text on the manufacturing part to indicate current dimensions or the like. Employing semantic lighting in the work place is likely to have a substantial impact in the worker comfort and productivity.

Vehicle Semantic Headlight:

In this application the semantic lighting system will deliver light that has the most effective and comfortable color, spectrum, intensity, focus, range and temperature for night driving. The subject 80 is the road ahead of the driver and any object that is in the path of the vehicle movement. The semantic lighting system 2 will take in consideration a particular driver night eye performance parameters, the subject temperature, infrared image, position, range, angle, contrast, texture, color, reflection and other visual properties that are related to driving. Based on the above considerations the Processing Unit 60 (PU) will analyze the data, build models for the subject and the user, and instruct the Programmable Light Unit 40 (PLU) to deliver appropriate light to each part of the subject, while taking in consideration the current regulation for headlight range, color and intensity. Since in one implementation Programmable Light Unit 40 (PLU) uses a combination of halogen, high intensity LED and data projection engines, the semantic light is obtained by a real time programmed combination of all three light sources. Programmable Light Unit 40 (PLU) also have the capability to project data directly on the subject. Since the sensor pod 30 (SP) continuously analyzes (both in visual and infrared spectrum) the change in lighting condition and the change of subject (such as new object in the path) the Programmable Light Unit 40 (PLU) light could change to focus light on an object of relevance (such as a deer in the path of the vehicle).

It should now be apparent that the foregoing semantic lighting system provides a dynamic, full customized, and automatic lighting profile to a subject by controlling that is optimized in spectrum, intensity, color, contrast, temperature, angle, focus, etc., for any given environment, subject and task. Moreover, the invention disclosed herein provides dynamic light that changes over time to adapt to changing environments and changing requirements of the task requiring illumination.

Having now fully set forth the preferred embodiments and certain modifications of the concept underlying the present invention, various other embodiments as well as certain variations and modifications thereto may obviously occur to those skilled in the art upon becoming familiar with the underlying concept. It is to be understood, therefore, that the invention may be practiced otherwise than as specifically set forth herein.

What is claimed is:

1. A semantic lighting system for delivering a dynamic, fully user personalized, and subject and task specific lighting profile to a subject, comprising:
    a programmable light unit for emitting a programmed pattern and spectra of illumination;
    a sensor pod comprising an array of sensors for detecting ambient lighting conditions plus characteristics of a subject to be illuminated;
    a control unit for allowing a user to program the lighting system; and
    a processing unit for analyzing data from said sensor pod and control unit and for constructing an optimal lighting profile in accordance therewith;
    whereby said lighting system generates light in accordance with said lighting profile that is optimized in spectrum, intensity, color, contrast, temperature, angle, and focus for any given user, environment, subject and task.

2. The semantic lighting system according to claim 1, wherein said sensor pod additionally senses characteristics of a human user for constructing said optimal lighting profile.

3. The semantic lighting system according to claim 2, wherein said human user characteristics include eye characteristics.

4. The semantic lighting system according to claim 2, wherein said human user characteristics include a relative position of the user with respect to the source of light.

5. A method for delivering a dynamic and task specific lighting profile to a subject, comprising the steps of:
    first analyzing properties of a subject, inclusive of nature, dimensions, shape, texture, contrast, reflectivity, transparence and temperature;
    second analyzing properties of environment, inclusive of existing illumination;
    controlling a lighting source in accordance with said first analysis and second analysis, and with one or more variables chosen from among the group including spectrum, intensity, color, contrast, temperature, angle, focus, and data;
    controlling said lighting source dynamically over time to adapt to changing environments and changing task requirements.

6. The method according to claim 5, further comprising a third step of analyzing characteristics of a human user, said step of controlling a lighting source being in accordance with said first analysis, second analysis and third analysis for constructing said optimal lighting profile.

7. The method according to claim 6, wherein said characteristics of a human user include eye characteristics.

8. The method according to claim 6, wherein said characteristics of a human user include a relative position of the user with respect to the source of light.

* * * * *